United States Patent
Xu et al.

(10) Patent No.: US 9,569,839 B2
(45) Date of Patent: Feb. 14, 2017

(54) IMAGE PROCESSING APPARATUS, METHOD AND MEDICAL IMAGE DEVICE

(71) Applicant: Toshiba Medical Systems Corporation, Otawara (JP)

(72) Inventors: Cui Xu, Beijing (CN); Heng Hu, Beijing (CN); Shigeharu Ohyu, Yaita (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/289,904

(22) Filed: May 29, 2014

(65) Prior Publication Data
US 2014/0355863 A1   Dec. 4, 2014

(30) Foreign Application Priority Data

May 29, 2013  (CN) .......................... 2013 1 0205674

(51) Int. Cl.
*G06K 9/00*      (2006.01)
*G06T 7/00*      (2006.01)
(Continued)

(52) U.S. Cl.
CPC ........... *G06T 7/0012* (2013.01); *A61B 5/0263* (2013.01); *A61B 5/4244* (2013.01); *A61B 6/481* (2013.01);
(Continued)

(58) Field of Classification Search
CPC ..... A61B 6/507; A61B 5/026; A61B 5/02028; G06F 19/3437
See application file for complete search history.

(56) References Cited

U.S. PATENT DOCUMENTS 6,745,066 B1 *  6/2004  Lin .................. A61B 6/481
                                                              378/4
7,069,068 B1 *  6/2006  Ostergaard ........ A61B 6/507
                                                              324/307
(Continued)

FOREIGN PATENT DOCUMENTS

| CN | 101506842 A | 8/2009 |
| CN | 101658425 A | 3/2010 |
| CN | 101658428 A | 3/2010 |

OTHER PUBLICATIONS

Bogunovic, Hrvoje. "Blood flow analysis from angiogram image sequence."*

(Continued)

*Primary Examiner* — Kim Vu
*Assistant Examiner* — Jonathan S Lee
(74) *Attorney, Agent, or Firm* — Oblon, McClelland, Maier & Neustadt, L.L.P.

(57) ABSTRACT

An image processing apparatus according to an embodiment includes an input extraction unit, and a parameter estimation unit. The input extraction unit configured to extract, from time sequence images of medical images obtained by performing a blood perfusion imaging scan on a tissue, a region where a main vessel supplying blood input to the tissue is located as an input part and obtain, based on the input part, a time-density sequence of the blood input as an input time sequence. The parameter estimation unit configured to estimate parameters in a model representing the change of the blood flow at each point in the tissue with the input time sequence, based on the input time sequence, the model and the time sequence images, wherein the parameters include a delay undergone by the blood when flowing from the input part to each point in the tissue.

12 Claims, 6 Drawing Sheets

(51) Int. Cl.
*G06T 7/20* (2006.01)
*A61B 6/00* (2006.01)
*A61B 5/026* (2006.01)
*A61B 5/00* (2006.01)
*A61B 6/03* (2006.01)
*G01R 33/563* (2006.01)

(52) U.S. Cl.
CPC ............... *A61B 6/486* (2013.01); *A61B 6/507* (2013.01); *G06T 7/2053* (2013.01); *A61B 6/032* (2013.01); *A61B 6/037* (2013.01); *A61B 2576/02* (2013.01); *G01R 33/56366* (2013.01); *G06T 2207/30056* (2013.01); *G06T 2207/30104* (2013.01)

(56) References Cited

U.S. PATENT DOCUMENTS

| | | | | |
|---|---|---|---|---|
| 2006/0083687 | A1* | 4/2006 | Yang | A61B 5/0263 424/9.3 |
| 2007/0255135 | A1* | 11/2007 | Kalafut | A61B 5/02028 600/431 |
| 2008/0300484 | A1* | 12/2008 | Wang | G06F 19/3437 600/431 |
| 2009/0297008 | A1* | 12/2009 | Taxt | G06T 7/0012 382/131 |
| 2010/0030073 | A1* | 2/2010 | Kalafut | A61B 6/481 600/431 |
| 2010/0060644 | A1* | 3/2010 | Elie | A61B 8/481 345/440 |
| 2010/0183207 | A1* | 7/2010 | Sakaguchi | A61B 6/507 382/128 |
| 2011/0130668 | A1* | 6/2011 | Ohyu | A61B 5/0263 600/504 |
| 2012/0323118 | A1* | 12/2012 | Menon Gopalakrishna | A61B 6/463 600/431 |
| 2013/0039553 | A1* | 2/2013 | Kjolby | A61B 5/026 382/128 |
| 2013/0261445 | A1* | 10/2013 | Ertel | A61B 5/0044 600/431 |
| 2014/0086461 | A1* | 3/2014 | Yao | A61B 6/032 382/128 |
| 2014/0254909 | A1* | 9/2014 | Carmi | A61B 6/032 382/131 |

OTHER PUBLICATIONS

Salluzzi, Marina, Richard Frayne, and Michael R. Smith. "An alternative viewpoint of the similarities and differences of SVD and FT deconvolution algorithms used for quantitative MR perfusion studies." Magnetic resonance imaging 23.3 (2005): 481-492.*

Bernstine, Hanna, et al. "FDG PET/CT early dynamic blood flow and late standardized uptake value determination hepatocellular carcinoma." Radiology 260.2 (2011): 503-510.*

Charles A. Cuenod, et al., "Deconvolution Technique for Measuring Tissue Perfusion by Dynamic CT: Application to Normal and Metastatic Liver" Academic Radiology, vol. 9, Suppl. 1, 2002, S205-S211.

Cheng Liuquan, et al., "Experimental Study on Hepatic Perfusion by CT", Chinese J. Med. Imaging vol. 10, No. 1, 2002, pp. 41 and 42 (with English translation).

Combined Chinese Office Action and Search Report issued on Jul. 22, 2016 in Patent Application No. 201310205674.0 (with English translation).

Cheng Liuquan, et al.. "Experimental Study on Hepatic Perfusion by CT", Chinese J. Med. Imaging vol. 10, No. 1, 2002, pp. 41 and 42 (with English translation).

* cited by examiner

IMAGE PROCESSING APPARATUS, METHOD AND MEDICAL IMAGE DEVICE

CROSS-REFERENCE TO RELATED APPLICATIONS

This application is based upon and claims the benefit of priority from Chinese Patent Application No. 201310205674.0, filed on May 29, 2013, the entire contents of which are incorporated herein by reference.

FIELD

Embodiments described herein relate generally to image processing and more particularly to an image processing apparatus, an image processing method and a medical image device.

BACKGROUND

In the field of image processing, processing a directly obtained image to obtain parameters related to an examined object is an important application, which generally involves an accurate modeling of the examined object. Specifically, an input region and an object region may be included in the obtained image, wherein the input region acts on the object region through a certain mechanism to obtain a corresponding output and/or an observable change in a certain state of the object region. This is equivalent to a response of the object region to the input, the response reflecting features of the object region. In the case where the input and the state change are known, a specific model can be constructed to obtain parameters reflecting the features of the object region.

For instance, in the processing of a medical image, it is usually required to process a series of images obtained by scanning to obtain physiological parameters of a related tissue or organ. Taking the blood perfusion imaging of the liver as an example, a selected slice is dynamically scanned after the intravenous bolus injection of contrast medium to obtain the time-density curve (TDC) of each pixel in this slice. Various perfusion parameters such as a hepatic artery perfusion (HAP), a hepatic portal perfusion (HPP) and a hepatic perfusion index (HPI), are calculated using different mathematical models according to the curve, and a perfusion image is formed through color level assignment to study the blood perfusion feature and the vascular characteristics of an organ and a lesion.

DETAILED DESCRIPTION

A brief summary of the present invention is given below to provide a basic understanding of some aspects of the present invention. It should be appreciated that the summary, which is not an exhaustive overview of the present invention, is not intended to identify the key or critical parts of the present invention nor limit the scope of the present invention, but merely to present some concepts in a simplified form as a prelude to the more detailed description that is discussed later.

It is an object of the present invention to provide an image processing apparatus, an image processing method and a medical image device which process an image to obtain more accurate modeling and parameter estimation concerning the examined object.

In accordance with an aspect of the embodiments, there is provided an image processing apparatus comprising: an input extraction unit configured to extract, from time sequence images of medical images obtained by performing a blood perfusion imaging scan on a tissue, a region where a main vessel supplying blood input to the tissue is located as an input part and obtain, based on the input part, a time-density sequence of the blood input as an input time sequence; and a parameter estimation unit configured to estimate parameters in a model representing the change of the blood flow at each point in the tissue with the input time sequence, based on the input time sequence, the model and the time sequence images, wherein the parameters include a delay undergone by the blood when flowing from the input part to each point in the tissue.

In accordance with another aspect of the present invention, a medical image device comprises the image processing apparatus according to the above aspects of the present invention.

In accordance with still another aspect of the present invention, there is provided an image processing method comprising: extracting, from time sequence images of medical images obtained by performing a blood perfusion imaging scan on a tissue, a region where a main vessel supplying blood input to the tissue is located as an input part and obtaining, based on the input part, a time-density sequence of the blood input as an input time sequence; and estimating parameters in a model representing the change of the blood flow at each point in the tissue with the input time sequence, based on the input time sequence, the model and the time sequence images, wherein the parameters comprise a delay undergone by the blood when flowing from the input part to each point in the tissue.

Further, in accordance with yet another aspect of the present invention, there is provided a computer program for realizing the aforementioned image processing method.

Additionally, in accordance with yet still another aspect of the present invention, there is provided a computer program product in the form of a medium at least readable to a computer, on which computer program codes for realizing the aforementioned image processing method are recorded.

In the image processing method, image processing apparatus and medical image device disclosed herein, by taking the delay undergone by the blood when flowing from a feeding artery to each point in a tissue into consideration, more accurate modeling and more accurate estimation on various physiological parameters can be performed on the blood flow of the tissue.

Embodiments of the invention are described below with reference to accompanying drawings. The elements and features described in one of the accompanying drawings or embodiments of the present invention may be combined with those shown in one or more other accompanying drawings or embodiments. It should be noted that for the sake of clarity, the representation and description on the components and processing that are irrelative with the present invention but well known by those skilled in the art are omitted.

Figure 1:
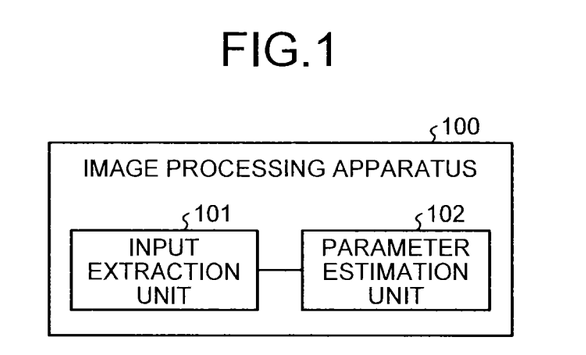
FIG. 1 is a block diagram illustrating the structure of an image processing apparatus according to an embodiment of the present invention.

As shown in FIG. 1, the image processing apparatus 100 according to an embodiment of the present invention structurally comprises an input extraction unit 101 and a parameter estimation unit 102. The input extraction unit 101 is configured to extract, from time sequence images of medical images obtained by performing a blood perfusion imaging scan on a tissue, a region where a main vessel supplying blood input to the tissue is located as an input part and obtain, based on the input part, the time-density sequence of the blood input as an input time sequence. The parameter estimation unit 102 is configured to estimate parameters in a model representing the change of the blood flow at each point in the tissue with the input time sequence, based on the input time sequence, the model and the time sequence images, wherein the parameters include the delay undergone by the blood when flowing from the input part to each point in the tissue.

The medical image mentioned here may be an image formed from the examinee's data obtained using a medical diagnostic imaging device. The medical diagnostic device includes but is not limited to: a computer tomography (CT) apparatus, a magnetic resonance imaging (MRI) diagnostic apparatus and the like.

In the modern medicine, usually, one or more slices are dynamically and continuously scanned at a high speed several or tens of seconds after a proper amount of contrast medium is intravenous bolus injected so as to collect a series of images of the same slice which varies with the time, and a perfusion image is formed through color level assignment to study the blood perfusion feature and vascular characteristics of an organ and a lesion.

Regions of interest (ROI) of a tissue and a feeding artery are included in these images. The input extraction unit 101 extracts a ROI of the feeding artery as an input part, wherein the region may be located on the examined object or outside thereof. In addition, the extraction may be performed manually or automatically. Specifically, the input extraction unit 101 extracts the regions where this input part is located in each time sequence image, and processes the region to obtain an input at a corresponding time point, thereby further obtaining the distribution of the blood input over time.

As the ROI of the feeding artery is generally represented as a region rather than one pixel point, the pixel values of the region can be averaged or subjected to a weighted average processing and the like when acquiring the input time sequence. The pixel value refers to, for example, the gray-scale of each pixel point or the RGB value of a color image.

In addition, in the case of few images, the input extraction unit 101 can further perform interpolation on the obtained input time sequence using various existing interpolation algorithms, which include but are not limited to various curve fittings and linear interpolations.

During a scanning process, blood (containing the contrast medium) flows from a feeding artery to each part of the tissue, and the change in the pixel values of the obtained ROI of the tissue, which reflects the dynamic condition of the blood flowing in the tissue, can be deemed as a response of the tissue to an input part. Time-density curves (TDC) of the input part and the tissue are obtained based on the series of images, respectively, and then a desired physiological parameter, such as the blood flow of the tissue, can be obtained by estimating based on a model (or a transfer function) representing the change of the blood flow of each point in the tissue with the input time sequence.

It should be noted that due to the limitation in the image capturing speed, the TDC mentioned here is actually not a directly-obtained continuous curve over time but a fitted curve, in other words, the aforementioned time-density sequence is the discrete form of the TDC.

The parameter estimation unit 102 is configured to estimate the parameters in the model based on the input time sequence, the model and the time sequence images. The distribution of the desired parameters can be directly or indirectly obtained after the parameters are estimated.

In an embodiment of the present invention, the parameters of the model include the delay undergone by the blood when flowing from the input part to each point in the tissue. By including such a parameter, the model can reflect the flowing condition of the blood flowing in from the feeding artery in the tissue more accurately, thereby obtaining more accurate estimation on physiological parameters to provide reference for the diagnosis or treatment.

Figure 2:
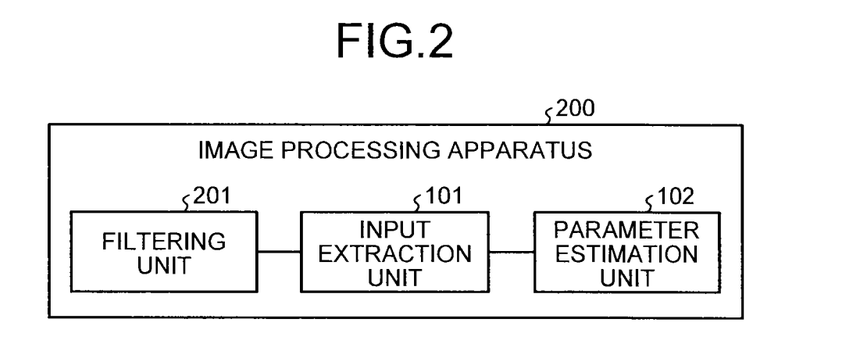
FIG. 2 is a block diagram illustrating the structure of an image processing apparatus according to another embodiment of the present invention.

In accordance with another embodiment of the present invention, as shown in FIG. 2, in addition to the input extraction unit 101 and the parameter estimation unit 102, the image processing apparatus 200 further comprises a filtering unit 201, which is configured to filter the time sequence images before they enters the input extraction unit 101 to reduce noises. The filtering may include both aspects of image filtering and time-domain filtering. For instance, a pixel averaging, a gauss filtering, a time-domain smoothing and the like can be performed. The filtering unit 201 can improve processing performance significantly, especially when the signal-to-noise ratio of an image is relatively low.

Figure 3:
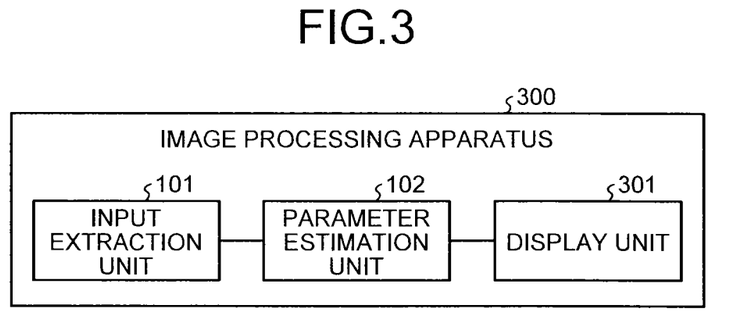
FIG. 3 is a block diagram illustrating the structure of an image processing apparatus according to still another embodiment of the present invention.

In accordance with another embodiment of the present invention, as shown in FIG. 3, in addition to the input extraction unit 101 and the parameter estimation unit 102, the image processing apparatus 300 further comprises a display unit 301, which is configured to generate and display the distribution diagram for each of the parameter so that the image processing apparatus 300 can provide an intuitive display for the user to facilitate the application. Although not shown in FIG. 3, the image processing apparatus 300 may further comprise the filtering unit 201.

Figure 4:
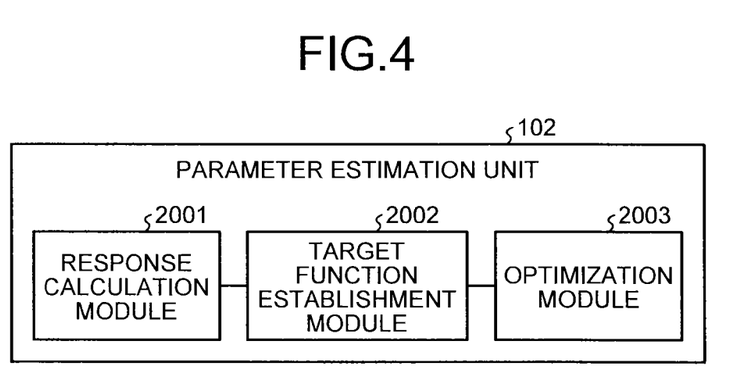
FIG. 4 is a block diagram illustrating the structure of a parameter estimation unit according to an embodiment of the present invention.

The structure and function of the parameter estimation unit 102 according to an embodiment of the present invention are described with reference to FIG. 4 below. As shown in FIG. 4, the parameter estimation unit 102 includes: a response calculation module 2001 configured to calculate the response of the model to the input time sequence; a target function establishment module 2002 configured to establish a target function using the difference between the response and the pixel values of the time sequence images; and an optimization module 2003 configured to optimize the target function to obtain each of the parameters in the model.

Specifically, the response calculation module 2001 calculates the response of the model of the tissue to the input time sequence $C_a(t)$ through a convolution operation. For the i-th pixel point, the response is as follows:

$$Q'(t)=FC_a(t-d_{ai}) \otimes R(t) \quad (1)$$

wherein $C_a(t)$ is the TDC of the feeding artery, $Q'(t)$ is the TDC of the tissue, $R(t)$ is the transfer function of the tissue, and $d_{ai}$ is the blood flow delay from the feeding artery to the i-th point in the tissue. By introducing the parameter $d_{ai}$ into the model, the time delay of the blood at the i-th point in the tissue with respect to in the feeding artery is compensated so that the model as well as the estimated parameters is more accurate.

Assuming $Q(t)$ represents the pixel value of the i-th pixel in the time sequence images, the target function establishment module 2002 establishes, using the difference $Q'(t)-Q(t)$, a target function, which may be for example the sum of squares of $Q'(t)-(t)$.

Then, the optimization module 2003 optimizes the above mentioned target function, for example, minimizes the sum of squares of $Q'(t)-Q(t)$.

In an embodiment, the optimization module 2003 is configured to optimize the target function using the nonlinear least square method.

It can be appreciated that the user can use the parameters resulting from the optimization as values most approximate to the actual physiological parameters of the tissue, and perform various analysis and judgment using the values.

It should be appreciated that although the processing on a medical image is described here by way of example, the description is merely exemplary, and in practice, the image processing apparatuses 100, 200 and 300 may be applied to analyzing and processing of images in various fields.

As another exemplary embodiment, the processing on images obtained from a blood perfusion imaging scanning on the liver is described below in detail. It should be appreciated that although the liver is described here as an example, an embodiment of the present invention may further be applied to other tissues or parts which are not limited to the liver.

Liver, as dually fed with blood by the hepatic artery and the portal vein, has two input parts. As it is difficult to recognize and thus accurately extract the region where the hepatic artery is located from a scanned image actually obtained, such as a CT image, therefore, the blood flow in the abdominal aorta positioned in the inner side of the spine, upstream of the hepatic artery is used as an input in the present application. Specifically, the input extraction unit 101 extracts regions of interest of the abdominal aorta and the portal vein from the time sequence images as an input part and obtains time-density sequences of the abdominal aorta and the portal vein. The extraction processing can be performed by manually circling the abdominal aorta region and the portal vein region and averaging the regions.

In actual implementation, as the human body can only bear a limited radiological dose, only a limited number of the time sequence images can be obtained. To reduce noises, the obtained time sequence images can be filtered. For example, the obtained time sequence images may be subjected to pixel binning, three-dimensional gauss filtering and the like.

Further, time-domain filtering, for example, smoothing over time, may be performed as well.

In another embodiment, the input extraction unit 101 is further configured to perform Gamma fitting of the time-density sequences of the abdominal aorta and the portal vein to interpolate, thereby obtaining more samples to improve the accuracy of the parameter optimization.

According to the studies on the detailed and effective hepatic circulation models, it is found that the hepatic circulation models can be simplified using a model based on a cumulative distribution function of the Gamma distribution, specifically, the following function may used as a transfer function $R(t)$ of the liver:

$$\begin{aligned} R(t) &= 1 - \Phi(t) \\ &= 1 - \int_0^t \phi(t)\,dt \\ &= 1 - P(nk, t/\theta) \\ &= 1 - \frac{\gamma(nk, t/\theta)}{\Gamma(nk)} \end{aligned} \quad (2)$$

wherein $\phi(t)$ is the probability density function of the Gamma distribution, $$\phi(t) = \frac{1}{\Gamma(nk)\theta^{nk}} t^{nk-1} \exp\left(-\frac{t}{\theta}\right).$$

It has been proved by experiments that by using the cumulative distribution function based on the Gamma distribution as a transfer function, the hemodynamics of the liver can be described more accurately. It should be appreciated that although a transfer function based on the Gamma function is described herein as an example, transfer functions of other types, such as the Weber function, can also be used.

Further, the relationship between the TDC of the liver tissue and the TDC of the input blood flow may be described with the following model:

$$C_T^*(t)=F[\alpha C_a(t-d_{ai})+(1-\alpha)C_p(t-d_{pi})] \otimes R(t) \quad (3)$$

wherein $\alpha$ refers to a hepatic perfusion index (HPI), F is the total hepatic blood flow, $C_a(t)$ is the TDC of the abdominal aorta, $C_p(t)$ is the TDC of the portal vein, $C_T^*(t)$ is the TDC of the liver tissue at the i-th point in the liver, $d_{ai}$ is the blood flow delay from the abdominal aorta to the i-th point in the liver, $d_{pi}$ is the blood flow delay from the portal vein to the i-th point in the liver, and $R(t)$ is a transfer function for the liver, as shown in equation (2).

Assuming that the TDC of the actual tissue at the i-th point of the liver obtained from the time sequence images is $C_T(t)$, then the following target function can be established:

$$F(x) = \sum_{m=1}^{N} f_m^2(x) = \sum_{m=1}^{N} (C_T(m\Delta t) - C_T^*(m\Delta t))^2 \quad (4)$$

Wherein, $m=1, \ldots, N$ represents different image capturing moments, and $\Delta t$ represents the time interval between the capturing timings of two adjacent images.

Subsequently, the above target function is minimized to obtain the respective parameters, including α, F, $d_{ai}$, $d_{pi}$ and parameters nk and θ of the Gamma distribution. These parameters may further include a hepatic artery perfusion (HAP), a hepatic portal perfusion (HPP), and the like.

The target function can be minimized using the nonlinear least square method which is advantageous in that even the minimal value far away from a starting value can be found. Of course, other optimization methods are also applicable.

During the scanning, for example, during CT scanning, the whole liver is sliced imaged, and each pixel point in each slice of image is subjected to the aforementioned processing to obtain the distribution of the parameters in each slice, thereby finally obtaining the three-dimensional (3D) distribution of the parameters in the whole liver.

In addition, in order to avoid the problem that there are so many parameters to be optimized that the algorithm cannot converge easily, the above mentioned $d_{pi}$ can be set to be a uniform value for all points of the whole liver tissue.

Figure 5A:
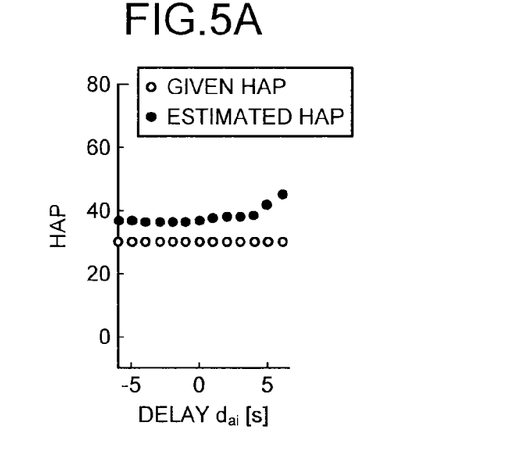
FIGS. 5A to 5C are comparison diagrams illustrating the hepatic perfusion parameters obtained by an image processing apparatus according to an embodiment of the present invention and given perfusion parameters.
Figure 5B:
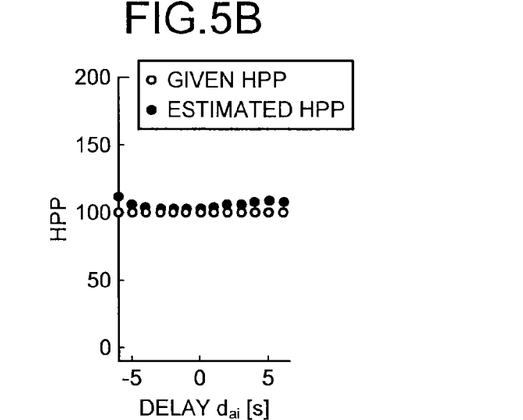
Figure 5C:
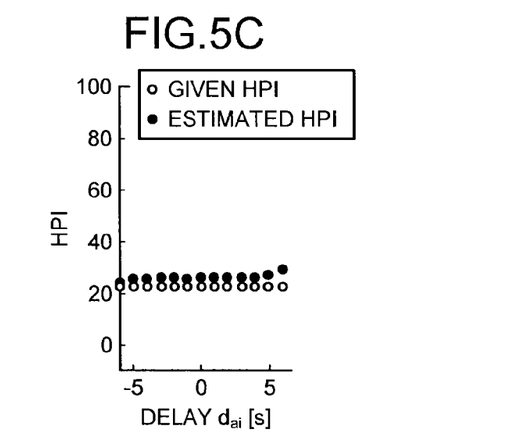
Figure 6A:
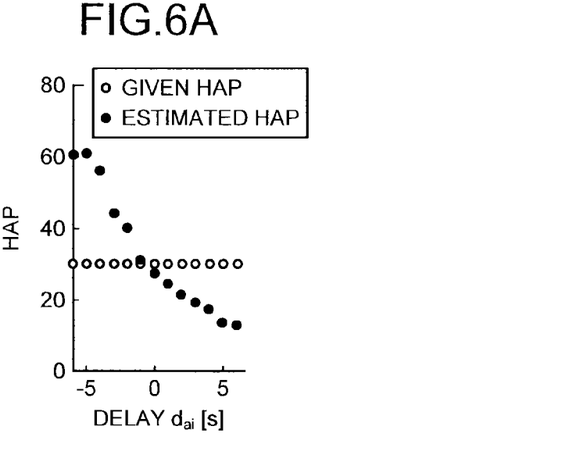
FIGS. 6A to 6C are comparison diagrams illustrating the hepatic perfusion parameters obtained by an image processing apparatus taking no consideration of delays of the abdominal aorta and the portal vein and given perfusion parameters.
Figure 6B:
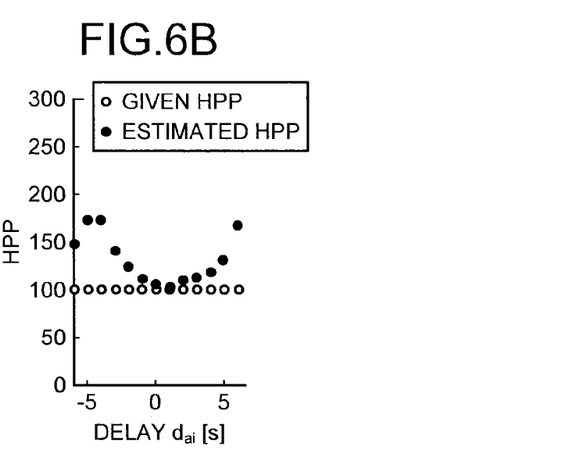
Figure 6C:
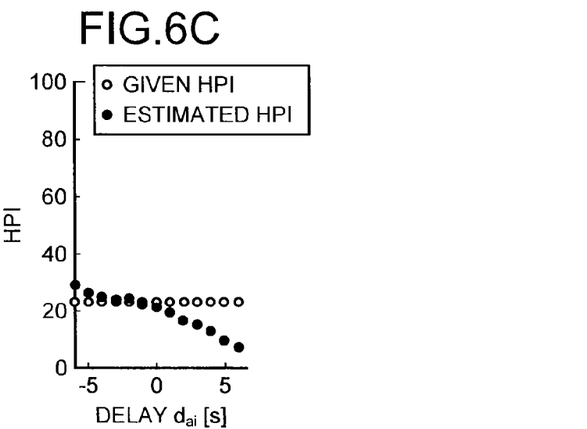

FIGS. 5A to 5C are comparison diagrams illustrating the hepatic perfusion parameters estimated by an image processing apparatus according to an embodiment of the present invention using the aforementioned algorithm and given perfusion parameters. At the same time, as a contrast, FIGS. 6A to 6C are diagrams illustrating the comparison of the hepatic perfusion parameters estimated with a algorithm taking no consideration of the delay $d_{ai}$ and $d_{pi}$ and corresponding given perfusion parameters, wherein the delay $d_{pi}$ is set to be a uniform value for the whole liver.

In FIGS. 5A to 5C and FIGS. 6A to 6C, the delay $d_{ai}$ varies in a range of −6 s to 6 s. Wherein, hollow points represent given perfusion parameters, and solid points represent the estimated perfusion parameters. As shown in FIGS. 6 A to 6C, in the case where an algorithm taking no consideration of the aforementioned delay is used, if the delay $d_{ai}$ is relatively great, the estimated perfusion parameters, including the HAP, the HPP and the HPI, are greatly deviated from the corresponding given perfusion parameters. However, as shown in FIGS. 5 A to 5C, when the aforementioned algorithm described in the application is adopted, relatively accurate estimation on perfusion parameters can be obtained across the whole delay range.

It has been proved by experiments that the image processing apparatus disclosed herein is less sensitive to noises, and can obtain a desired result even when the signal-to-noise ratio is, for example, 20 dB. Besides, the image processing apparatus disclosed herein is insensitive to cases and can obtain a desired result from all the tested cases though different individuals actually have different hepatic hemodynamics. As the model employed describes the hepatic hemodynamics well and the delays of the abdominal aorta and the portal vein are well compensated, accurate parameter estimation can be obtained. Further, when run on a general personal computer, the processing time of the image processing apparatus disclosed herein is about 10 s, which meets the requirements of diagnostic applications.

Besides, in order to make more accurate parameter estimation possible, aside from the above mentioned target function (a first target function), a second target function may be used for determining delay independently. For example, the target function establishment module 2002 establish the first target function using the above mentioned difference in a first period of the above mentioned input time sequence, and establish the second target function using the above mentioned difference in a second period containing the anterior half of the above mentioned input time sequence. Then, the optimization module 2003 minimizes the first target function and the second target function simultaneously. Here, the difference in the anterior half of TDC is used here because the degree of the delay tends to be reflected in measured values.

For example, the target function establishment module 2002 establish the sum of squares of the difference Q'(t)−Q(t) of a period from t1 to t2 after the contrast medium is injected as the first target function. Here, t1 is the measurement starting time of the TDC of the tissue, and t2 is the measurement termination time of the TDC of the tissue, for example. Moreover, the target function establishment module 2002 establish the sum of squares of the difference Q'(t)−Q(t) of a period from t3 to t4 after the contrast medium is injected as the second target function. Here, t3 is the time after several seconds after the measurement of the TDC of the tissue, and t4 is the time when the measured value of the TDC of the tissue reached the peak, for example.

Then, the optimization module 2003 minimizes the first target function and second target function simultaneously. For example, the optimization module 2003 repeats a process to obtain the above mentioned each of the parameters using the first target function, and a process to obtain the delay $d_{ai}$ using the second target function, so as to minimize these target functions simultaneously.

Specifically, first, the optimization module 2003 obtains each of the parameters by assigning the initial value of the delay $d_{ai}$ to the first target function, and obtains the delay $d_{ai}$ by assigning the initial value of each of the parameters to the second target function.

Then, the optimization module 2003 the optimization module 2003 obtains each of the parameters by assigning the delay $d_{ai}$ obtained last time by assigning the second target function to the first target function, and obtains the delay $d_{ai}$ by assigning each of the parameters obtained last time by assigning the first target function to the second target function.

As describe above, the optimization module 2003 repeats the process to obtain each of the parameters using the first target function, and the process to obtain the delay $d_{ai}$ using the second target function, and repeats assigning the value obtained by each target function to the mutual target function. And the optimization module 2003 ends processing of minimization, when the value obtained will not change a lot.

In addition, the processing in which the optimization module 2003 minimizes the first target function and second target function simultaneously is not limited to the above mentioned example. For example, the optimization module 2003 may minimize the value obtained by the function which carried out weighted addition processing of the first target function and second target function.

It is apparent that some processing or methods are also disclosed in the description above on the image processing apparatus according to embodiments of the present invention. Below, the summary of the methods is described without repeating the details which are already discussed above, however, it should be noted that although disclosed in the description of the image processing apparatus, the methods do not certainly employ or are not certainly executed by the aforementioned components. For instance, embodiments of the image processing apparatus may be partially or completely achieved by hardware and/or firmware, and the image processing methods described below may be fully achieved by a computer-executable program, although the image processing methods may employ the hardware and/or firmware of the image processing apparatus.

Figure 7:
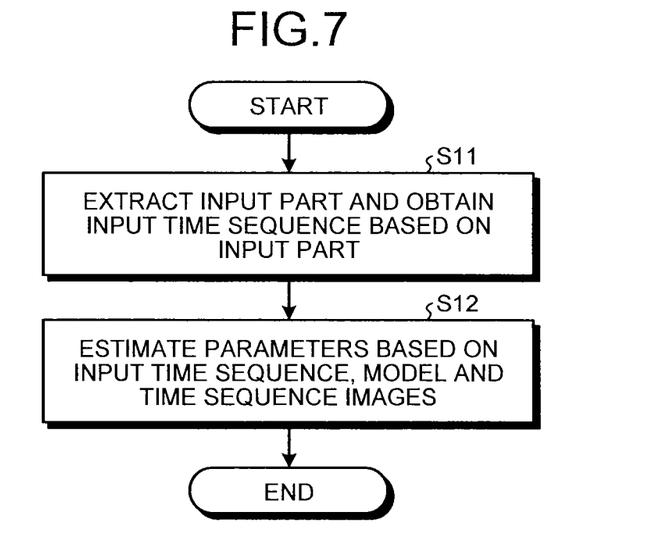
FIG. 7 is a flowchart illustrating an image processing method according to an embodiment of the present invention.

FIG. 7 shows a flowchart of an image processing method according to an embodiment of the present invention. The image processing method comprising: extracting, from time sequence images of medical images obtained by performing a blood perfusion imaging scan on a tissue, a region where a main vessel supplying blood input to the tissue is located as an input part and obtaining, based on the input part, a time-density sequence of the blood input as an input time sequence (S11); and estimating parameters in a model representing the change of the blood flow at each point in the tissue with the input time sequence, based on the input time sequence, the model and the time sequence images (S12), wherein the parameters include a delay undergone by the blood when flowing from the input part to each point in the tissue.

In the image processing method, Step S11 may be executed by the input extraction unit 101 arranged in the image processing apparatuses 100, 200 and 300 described herein, and Step S12 may be executed by the parameter estimation unit 102 arranged in the image processing apparatuses 100, 200 and 300 described herein.

Figure 8:
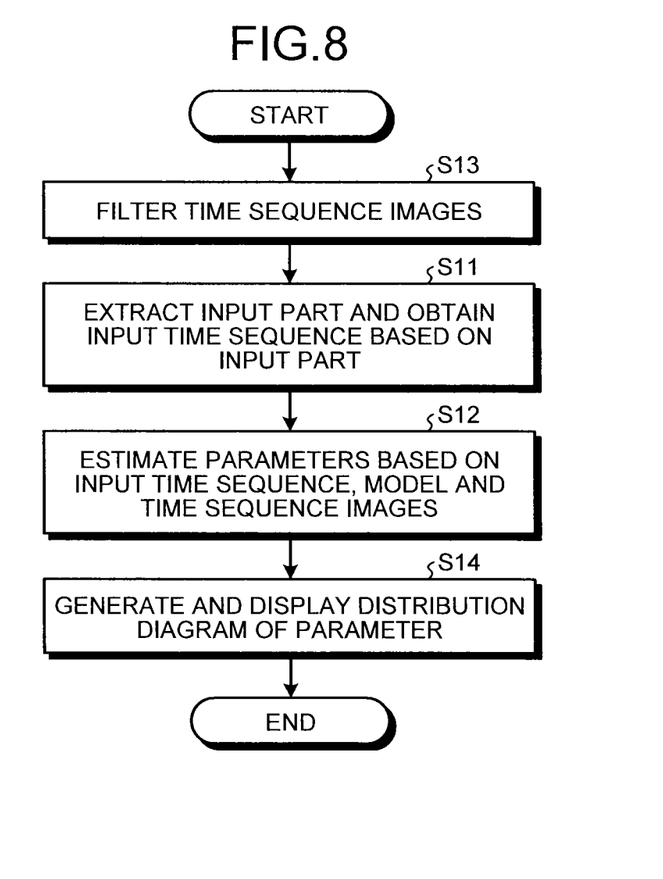
FIG. 8 is a flowchart illustrating an image processing method according to another embodiment of the present invention.

As shown in FIG. 8, an image processing method according to another embodiment of the present invention further comprises: filtering the time sequence images before the input part is extracted therefrom so as to reduce noises (S13). Step S13 may be executed by the filtering unit 201 arranged in the image processing apparatus 200, 300 described herein. Further, the image processing method may further include a step of generating and displaying the distribution diagram of each of the parameters (S14). Step S14 may be executed by the display unit 301 arranged in the image processing apparatus 300 described herein.

It should be noted that Steps S13 and S14 are optional, in other words, an image processing method including none of or either of or both of Steps S13 and S14 falls into the scope of the present application.

Further, the image processing method disclosed herein may further include a step of performing interpolation on the obtained input time sequence.

In an embodiment, the parameter estimation step S12 includes the following sub-steps of: calculating a response of the model to the input time sequence; establishing a target function using the difference between the response and the pixel values of the time sequence images; and optimizing the target function to obtain each of the parameters in the model.

In an embodiment, the target function may be optimized using the nonlinear least square method.

In an embodiment, the tissue is a liver. The model is based on a cumulative distribution function of the Gamma distribution.

In an embodiment, the image processing method comprises: extracting regions of interest of an abdominal aorta and a portal vein from the time sequence images as an input part and obtaining time-density sequences of the abdominal aorta and the portal vein. Moreover, the model includes the following delay parameters: a first delay from the abdominal aorta to each point in the liver tissue; and a second delay from the portal vein to each point in the liver tissue.

In an embodiment, the second delay is a uniform value for all points of the whole liver tissue.

In an embodiment, the aforementioned image processing method further includes performing interpolating by Gamma fitting of the time-density sequences of the abdominal aorta and the portal vein.

In an embodiment, the parameters further include a hepatic artery perfusion index, a hepatic artery perfusion, a hepatic portal perfusion and parameters of the Gamma distribution.

More specific details of each step of the image processing method and more possible steps of the image processing method may be understood with reference to the description on each component of the image processing apparatuses described above and are therefore not described in detail here.

It should be appreciated that the image processing apparatus and image processing method described herein are applicable to processing various images, for example, medical images.

Figure 9:
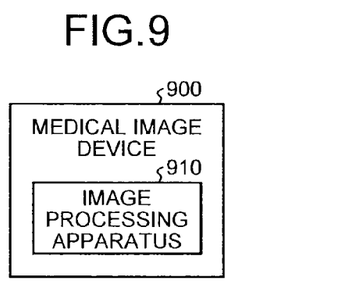
FIG. 9 is a schematic block diagram illustrating a medical image device according to an embodiment of the present invention.

FIG. 9 shows a schematic block diagram illustrating a medical image device according to an embodiment of the present invention. In order not to obscure the spirit and scope of the present invention, other possible components of the medical image device are omitted in FIG. 9. The medical image device 900 includes an image processing apparatus 910 for processing the input time sequence images. The image processing apparatus 910 may be the image processing apparatus 100, 200, or 300 described in any one of the embodiments above. The medical image device 900 may be, but not limited to: a X-ray imaging diagnostic device, an ultrasound (UL) diagnostic imaging device, a computer tomography (CT) device, a magnetic resonance imaging (MRI) diagnostic device, a positron emission tomography (PET) device or the like.

The image processing apparatus may be arranged in the medical image device in a specific way or manner that is well known to those skilled in the art and is therefore not described in detail herein.

As an example, each step of the aforementioned image processing method and each module and/or unit of the aforementioned image processing apparatus may be implemented as software, firmware, hardware or the combination thereof. In the case where the steps or modules and/or units are realized by software or firmware, a software program for realizing the above mentioned method may be installed in a computer with a dedicated hardware structure (e.g. the general computer 1000 shown in FIG. 10) from a storage medium or network, wherein the computer is capable of implementing various functions when installed with various programs.

Figure 10:
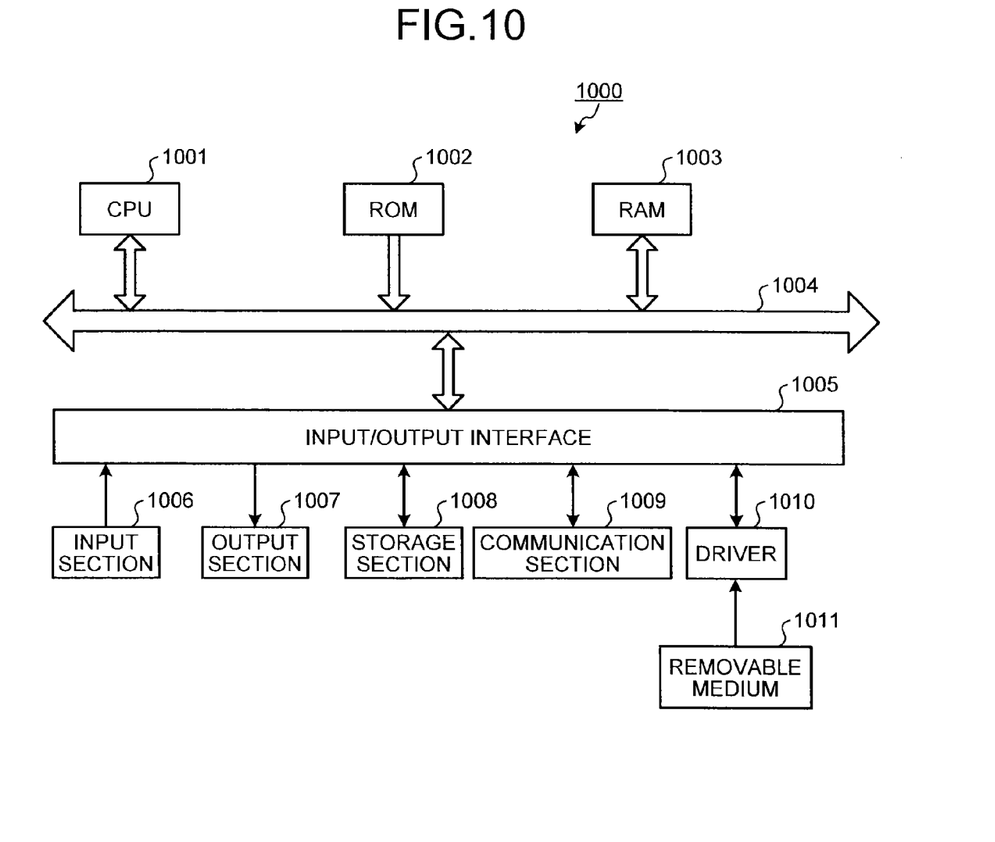
FIG. 10 is an exemplary block diagram illustrating the structure of a computer capable of realizing the embodiments/examples of the present invention.

In FIG. 10, a computing processing unit (namely, CPU) 1001 executes various processing according to a program stored in a read-only memory (ROM) 1002 or a program loaded to a random access memory (RAM) 1003 from a storage section 1008. The data needed for the various processing of the CPU 1001 may be stored in the RAM 1003 as needed. The CPU 1001, the ROM 1002 and the RAM 1003 are linked with each other via a bus 1004. An input/output interface 1005 is also linked to the bus 1004.

The following components are linked to the input/output interface 1005: an input section 1006 (including keyboard, mouse and the like), an output section 1007 (including displays such as cathode ray tube (CRT), a liquid crystal display (LCD), a loudspeaker and the like), a storage section 1008 (including hard disc and the like), and a communication section 1009 (including a network interface card such as a LAN card, modem and the like). The communication section 1009 performs communication processing via a network such as the Internet. A driver 1010 may also be linked to the input/output interface 1005, if needed. If needed, a removable medium 1011, for example, a magnetic disc, an optical disc, a magnetic optical disc, a semiconductor memory and the like, may be installed in the driver 1010 so that the computer program read therefrom is installed in the memory section 1008 as appropriate.

In the case where the foregoing series of processing is achieved through software, programs forming the software are installed from a network such as the Internet or a memory medium such as the removable medium 1011.

It should be appreciated by those skilled in the art that the memory medium is not limited to the removable medium 1011 shown in FIG. 10, which has program stored therein and is distributed separately from the apparatus so as to provide the programs to users. The removable medium 1011 may be, for example, a magnetic disc (including floppy disc (registered trademark)), a compact disc (including compact disc read-only memory (CD-ROM) and digital versatile disc (DVD), a magneto optical disc (including mini disc (MD) (registered trademark)), and a semiconductor memory. Alternatively, the memory medium may be the hard discs included in ROM 1002 and the storage section 1008 in which programs are stored, and can be distributed to users along with the device in which they are incorporated.

The present invention further discloses a program product in which machine-readable instruction codes are stored. The aforementioned image processing methods can be implemented when the instruction codes are read and executed by a machine.

Accordingly, a memory medium for carrying the program product in which machine-readable instruction codes are stored is also covered in the present invention. The memory medium includes but is not limited to soft disc, optical disc, magnetic optical disc, memory card, memory stick and the like.

In the foregoing description on the specific embodiments of the present invention, the features described and/or shown for an embodiment may be used in one or more other embodiments in the same or similar way or combined with those in the other embodiments, or replace those in the other embodiments.

It should be emphasized that the terms 'comprise/include', as used herein, means the existence of a feature, element, step or component in a way not exclusive of the existence or addition of one or more other features, elements, steps or components.

In the aforementioned embodiments and examples, each step and/or unit is represented with a reference sign consisting of figures. It should be understood by those of ordinary skill of the art that the reference signs are merely intended to facilitate description and drawing but are not to be construed as a limitation on an order or any other aspect.

Furthermore, the methods provided in the present invention may be performed sequentially, synchronously or independently in accordance with another time sequences, not limited to the time sequence described herein. Therefore, the implementation orders of the methods described in this specification are not to be construed as a limitation to the scope of the present invention.

Although the present invention has been disclosed with reference to specific embodiments herein, it should be understood that all the embodiments and examples described above are merely illustrative of the present invention but are not to be construed as limiting the present invention. Various modifications, improvements or equivalents can be devised by those skilled in the art without departing from the spirit and scope of the invention, and such modifications, improvements or equivalents should be considered to fall within the scope of the present invention.

What is claimed is:

1. An image processing apparatus, comprising:
processing circuitry configured to
   extract, from time sequence images of medical images obtained by performing a blood perfusion imaging scan on a liver, a region where a main vessel supplying blood input to the liver is located as an input part, and obtain, based on the input part, a time-density sequence of the blood input as an input time sequence, and
   estimate parameters introduced into a mathematical model representing a change of the blood flow at each point in the liver with the input time sequence, based on the input time sequence, the mathematical model, and the time sequence images, wherein the introduced parameters in the mathematical model include a delay undergone by the blood when flowing from the input part to each point in the liver, a hepatic artery perfusion index, a hepatic artery perfusion, a hepatic portal perfusion, and parameters of a Gamma distribution.

2. The image processing apparatus according to claim 1, wherein the processing circuitry is further configured to filter the time sequence images before extracting the region so as to reduce noise.

3. The image processing apparatus according to claim 1, wherein the processing circuitry is further configured to:
   calculate a response of the mathematical model to the input time sequence;
   establish a target function using the difference between the response and pixel values of the time sequence images; and
   optimize the target function to obtain each of the parameters in the mathematical model.

4. The image processing apparatus according to claim 3, wherein the processing circuitry is further configured to:
   establish a first target function using the difference in a first period of the input time sequence, and establish a second target function using the difference in a second period containing an anterior half of the input time sequence, and
   minimize the first target function and the second target function simultaneously.

5. The image processing apparatus according to claim 1, further comprising a display configured to generate and display a distribution diagram for each parameter.

6. The image processing apparatus according to claim 1, wherein the processing circuitry is further configured to perform interpolation on the input time sequence.

7. The image processing apparatus according to claim 1, wherein the mathematical model is based on a cumulative distribution function of the Gamma distribution.

8. The image processing apparatus according to claim 1, wherein
   the processing circuitry is further configured to extract, from the time sequence images, regions of interest of an abdominal aorta and a portal vein as the input part and obtain time-density sequences of the abdominal aorta and the portal vein; and
   the mathematical model includes a first delay from the abdominal aorta to each point in the liver, and a second delay from the portal vein to each point in the liver.

9. The image processing apparatus according to claim 8, wherein the second delay is a uniform value for all points of a whole of the liver.

10. The image processing apparatus according to claim 8, wherein the processing circuitry is further configured to perform interpolation by Gamma fitting of time-density sequences of the abdominal aorta and the portal vein.

11. An image processing method, comprising:

extracting, using processing circuitry, from time sequence images of medical images obtained by performing a blood perfusion imaging scan on a liver, a region where a main vessel supplying blood input to the liver is located as an input part, and obtaining, based on the input part, a time-density sequence of the blood input as an input time sequence; and estimating, using the processing circuitry, parameters introduced into a mathematical model representing a change of the blood flow at each point in the liver with the input time sequence, based on the input time sequence, the mathematical model, and the time sequence images, wherein the introduced parameters in the mathematical model include a delay undergone by the blood when flowing from the input part to each point in the liver, a hepatic artery perfusion index, a hepatic artery perfusion, a hepatic portal perfusion, and parameters of a Gamma distribution.

12. A medical image device, comprising an image processing apparatus, wherein the image processing apparatus includes:

processing circuitry configured to extract, from time sequence images of medical images obtained by performing a blood perfusion imaging scan on a liver, a region where a main vessel supplying blood input to the liver is located as an input part, and obtain, based on the input part, a time-density sequence of the blood input as an input time sequence, and estimate parameters introduced into a mathematical model representing a change of the blood flow at each point in the liver with the input time sequence, based on the input time sequence, the mathematical model, and the time sequence images, wherein the introduced parameters in the mathematical model include a delay undergone by the blood when flowing from the input part to each point in the liver, a hepatic artery perfusion index, a hepatic artery perfusion, a hepatic portal perfusion, and parameters of a Gamma distribution.

* * * * *